United States Patent [19]

Blahak et al.

[11] 4,022,720
[45] May 10, 1977

[54] PROCESS FOR THE PRODUCTION OF POLYURETHANE FOAMS

[75] Inventors: Johannes Blahak, Cologne; Hans-Joachim Meiners, Leverkusen-Schlebusch, both of Germany

[73] Assignee: Bayer Aktiengesellschaft, Leverkusen, Germany

[22] Filed: May 21, 1975

[21] Appl. No.: 579,522

[30] Foreign Application Priority Data

May 25, 1974 Germany .......................... 2425448

[52] U.S. Cl. .................. 260/2.5 AC; 260/77.5 AC; 260/482 B; 260/561 R
[51] Int. Cl.² .................. C07C 97/02; C08G 18/18
[58] Field of Search ... 260/2.5 AC, 75 NC, 77.5 AC, 260/482 B, 561 R

[56] References Cited

UNITED STATES PATENTS

| | | | |
|---|---|---|---|
| 3,644,490 | 2/1972 | Schmelzer et al. | 260/482 B |
| 3,714,249 | 1/1973 | Norton | 260/561 R |
| 3,922,238 | 11/1975 | Narayan et al. | 260/2.5 AC |

FOREIGN PATENTS OR APPLICATIONS

545,416  8/1957  Canada ...................... 260/77.5 AC

*Primary Examiner*—Donald E. Czaja
*Assistant Examiner*—H. H. Fletcher
*Attorney, Agent, or Firm*—Gene Harsh; Joseph C. Gil

[57] ABSTRACT

The present invention relates to a process for the production of polyurethane foams by reacting
1. organic compounds with at least two hydrogen atoms capable of reacting with isocyanates and having molecular weights in the range from 400 to 10,000,
2. polyisocyanates,
3. water and/or organic blowing agents in the presence of catalysts containing tertiary nitrogen and, optionally, other additives, the improvement wherein the catalysts used are polyacyl compounds corresponding to the general formula:

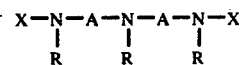

wherein
A represents a $C_1$–$C_6$ alkylene group, preferably a $C_2$ or $C_3$ alkylene group;
R represents a $C_1$–$C_5$ alkyl group, preferably methyl or ethyl;
X represents an acyl group, preferably

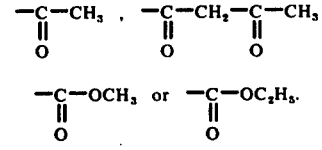

10 Claims, No Drawings

PROCESS FOR THE PRODUCTION OF POLYURETHANE FOAMS

BACKGROUND OF THE INVENTION

For some time now, polyurethane foams with a variety of different physical properties have been commercially produced by the isocyanate polyaddition process from compounds containing several active hydrogen atoms. Generally, such foams are produced from compounds containing hydroxyl and/or carboxyl groups, and polyisocyanates, in the presence of water and/or organic blowing agents and, optionally, catalysts, emulsifiers and other additives (Angew. Chem. A, 59 (1948), page 257). It is possible by suitably selecting the components to obtain both elastic and rigid foams and any intermediate between these two extremes.

Polyurethane foams are preferably obtained by mixing liquid components. Thus, in general, the starting materials to be reacted with one another are either simultaneously mixed, or an NCO-group-containing prepolymer is initially prepared and subsequently foamed.

Tertiary amines have proved to be effective catalysts in the production of polyurethane foams particularly because they are able to accelerate both the reaction between hydroxyl groups and/or carboxyl groups and the NCO-groups, and the reaction between water and the isocyanate groups, with the result that, in the one-shot process, the concurrent reactions may be adapted to one another.

In addition, the foaming process is accompanied by additional crosslinking reactions which result in the formation of allophanate, biuret and cyanurate structures. In view of the complexity of the reactions, it is necessary on the one hand to guarantee their synchronous completion by selecting suitable catalysts and, on the other hand, to ensure that the catalyst is not prematurely fixed by incorporation in the foam or does not subsequently interfere with hydrolytic degradation of the finished foam. In addition, the odor of numerous, commonly used tertiary amines is unfavorable for use in foams.

DESCRIPTION OF THE INVENTION

The present invention relates to a process for the production of polyurethane foams by reacting (1) organic compounds with at least two hydrogen atoms capable of reacting with isocyanates and having molecular weights in the range from 400 to 10,000, (2) polyisocyanates, (3) water and/or organic blowing agents in the presence of catalysts containing tertiary nitrogen and, optionally, other additives, the improvement wherein the catalysts used are polyacyl compounds corresponding to the general formula:

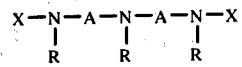

wherein
A represents a $C_1$-$C_6$ alkylene group, preferably a $C_2$ or $C_3$ alkylene group;
R represents a $C_1$-$C_5$ alkyl group, preferably methyl or ethyl;
X represents an acyl group, preferably

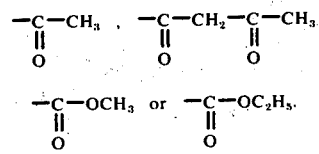

The catalysts used in accordance with the invention may be obtained by reacting known amines corresponding to the formula:

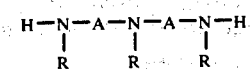

wherein
R and A are as defined above, with acylating agents, such as acid anhydrides, acid chlorides, diketene and dicarbonic acid esters, in a known manner (see, e.g. Organikum, VEB Deutscher Verlag der Wissenschaften, Berlin 1965).

The compounds corresponding to the formulae:

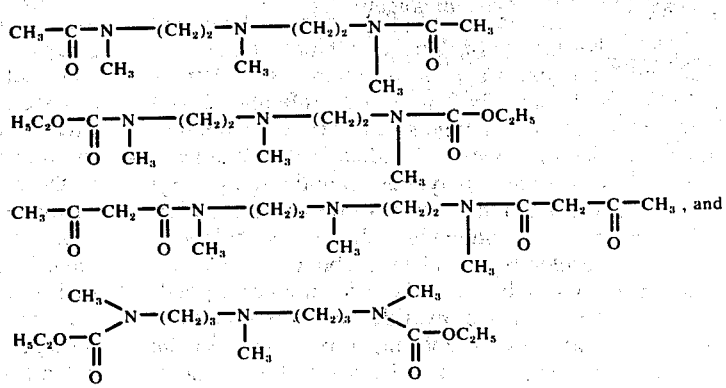

are novel compounds which also form part of the present invention.

The catalysts used in accordance with the invention are distinguished by the surprisingly intense accelerating effect which they have upon the foaming reaction, and by the fact that foams produced using them are odorless and show favorable hydrolysis behavior. As alkylamides or alkylurethanes, they are not incorporated by means of main valency bonds and, for this reason, remain active throughout the entire foaming reaction. The following are typical examples of the compounds according to the invention:

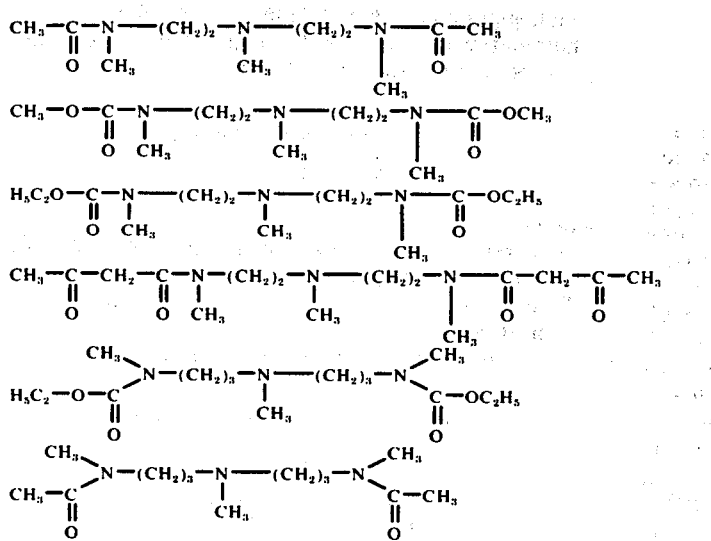

The first, fourth, fifth and sixth compounds above are preferred.

The catalysts according to the invention are generally used in quantities of from 0.01 to 5% by weight, and preferably in quantities of from 0.01 to 1% by weight, based on the total weight of the foamable reaction mixture.

As is known in the art, compounds useful in preparing polyurethane foams include organic compounds with at least two hydrogen atoms capable of reacting with isocyanates and having molecular weights of from 400 to 10,000. Apart from compounds containing amino groups, thiol groups or carboxyl groups, compounds of this type which are preferred are polyhydroxyl compounds. Particularly, preferred compounds are those containing 2 to 8 hydroxyl groups, and especially those with molecular weights of from 800 to 10,000 (most preferably 1,000 to 6,000). Examples include, polyesters, polyethers, polythioethers, polyacetals, polycarbonates and polyesteramides containing at least 2 and generally 2 to 8 and preferably 2 to 4 hydroxyl groups, of the type known per se for the production of homogeneous and cellular polyurethanes.

Examples of suitable polyesters containing hydroxyl groups include reaction products of polyhydric, preferably dihydric, and, optionally, trihydric alcohols with polyvalent, preferably divalent carboxylic acids. Instead of the free polycarboxylic acids the corresponding polycarboxylic acid anhydrides or esters with lower alcohols or mixtures thereof may also be used for the production of the polyesters. The polycarboxylic acids may be aliphatic, cycloaliphatic, aromatic and/or heterocyclic, and may optionally be substituted, for example, by halogen atoms, and/or they may be unsaturated. Examples of these polycarboxylic acids are succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorphthalic acid anhydride, endomethylene tetrahydrophthalic acid anhydride, glutaric acid anhydride, maleic acid, maleic acid anhydride, fumaric acid, dimeric and trimeric fatty acids, such as oleic acid, optionally in admixture with monomeric fatty acids, terephthalic acid dimethyl ester, terephthalic acidbis-glycol ester. Examples of suitable polyhydric alcohols include ethylene glycol, 1,2- and 1,3-propylene glycol, 1,4- and 2,3-butylene glycol, 1,6-hexane diol, 1,8-octane diol, neopentyl glycol, cyclohexane dimethanol (1,4-bishydroxymethyl-cyclohexane), 2-methyl-1,3-propane diol, glycerol, trimethylol-propane, 1,2,6-hexane triol, 1,2,4-butane triol, trimethylolethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutylene glycol and polybutylene glycols. The polyesters may contain terminal carboxyl groups. Polyesters of lactones, for example, ε-caprolactone, or hydroxycarboxylic acids, for example, ω-hydroxycaproic acid, may also be used.

The polyethers containing at least two and usually two to eight, and preferably two to three hydroxyl groups suitable for use in accordance with the invention, include those obtained by the polymerization of epoxides, such as ethylene oxide, propylene oxide, butylene oxide, tetrahydrofuran, styrene oxide or epichlorohydrin, for example, in the presence of $BF_3$, or by the chemical addition of these epoxides to starting components with reactive hydrogen atoms, such as water, ethylene glycol, 1,3- or 1,2-propylene glycol, trimethylolpropane, 4,4'-dihydroxydiphenylpropane, aniline, ammonia, ethanolamine and ethylene diamine. Sucrose polyethers of the type described in German Auslegeschrift Nos. 1,176,358 and 1,064,938 are also suitable for the purposes of the invention. In many cases, it is preferred to use polyethers of the type which predominantly contain primary OH-groups (up to 90% by weight based on all the OH-groups present in the polyether). Polyethers modified by vinyl monomers of the type obtained, for example, by the polymerization of styrene and acrylonitrile in the presence of polyethers (U.S. Pat. Nos. 3,383,351; 3,304,273; 3,523,093; 3,110,695 and German Pat. No. 1,152,536) are also suitable, as are polybutadienes containing OH-groups.

Among the polythio-ethers usable are included the condensation products of thiodiglycol with itself and/or with other glycols, dicarboxylic acids, formaldehyde, aminocarboxylic acids or aminoalcohols. Depending on the co-components, these products are polythiomixed ethers, polythio-ether esters or polythio-ether ester amides.

Suitable polyacetals include those compounds which may be obtained from glycols, such as diethylene glycol, triethylene glycol, 4,4'-dioxethoxy diphenyl-dimethyl methane and hexane diol, and formaldehyde. Polyacetals suitable for the purposes of the invention may also be obtained by polymerizing cyclic acetals.

Suitable polycarbonates containing hydroxyl groups include those obtainable by reacting diols, such as 1,3-propane diol, 1,4-butane diol and/or 1,6-hexane diol, diethylene glycol, triethylene glycol and tetraethylene glycol, with diarylcarbonates, such as diphenylcarbonate or phosgene.

Examples of polyester amides and polyamides include the predominantly linear condensates obtained from polyvalent saturated and unsaturated carboxylic acids or their anhydrides and polyhydric saturated and unsaturated amino alcohols, diamines, polyamines and mixtures thereof.

Polyhydroxyl compounds already containing urethane or urea groups and modified natural polyols, such as castor oil, carbohydrates and starch, may also be used. The addition productsof alkylene oxides with phenol-formaldehyde resins or even with urea-formaldehyde resins may also be used in accordance with the invention.

According to the invention, it is also possible to use known chain extenders and crosslinkers with molecular weights in the range of from 60 to 400, such as polyols, aminoalcohols or polyamines.

Representatives of the many different types of active hydrogen containing compounds suitable for use in accordance with the invention are described, for example, in High Polymers, Vol. XVI, "Polyurethanes, Chemistry and Technology" by Saunders-Frisch, Interscience Publishers, New York, London Vol. I, 1962, pages 32 to 42 and pages 44 to 54, and Vol. II, 1964, pages 5 to 6 and 198 and 199, and in Kunststoff-Handbuch, Vol. VII, Vieweg-Hochtlen, Carl-Hanser-Verlag Munich, 1966, pages 45 to 71.

The isocyanates suitable for the process according to the invention include essentially any organic polyisocyanate such as aliphatic, cycloaliphatic, araliphatic, aromatic and heterocyclic polyisocyanates of the type described, for example, by W. Siefken In Justus Liebigs Annalen der Chemie, 562, pages 75 to 136. Specific examples include ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate, and mixtures of these isomers; 1-isocyanato-3,3,5-trimethyl-5-isocyanatomethyl-cyclohexane (German Auslegeschrift 1,202,785); 2,4- and 2,6-hexahydrotolylene diisocyanate, and mixtures of these isomers; hexahydro-1,3- and/or 1,4-phenylene diisocyanate; perhydro-2,4' and/or -4,4'-diphenylmethane diisocyanate; 1,3- and 1,4-phenylene diisocyanate; 2,4- and 2,6-tolylene diisocyanate, and mixtures of these isomers; diphenylmethane 2,4'- and/or -4,4'-diisocyanate; naphthylene-1,5-diisocyanate; triphenylmethane-4,4',-4''-triisocyanate; polyphenylpolymethylene polyisocyanates of the type obtained by condensing aniline with formaldehyde, followed by phosgenation and described, for example, in the British Pat. Nos. 874,430 and 848,671; perchlorinated arylpolyisocyanates of the type described, for example, in German Auslegeschrift No. 1,157,601; polyisocyanates containing carbodiimide groups of the type described in German Pat. No. 1,092,007; diisocyanates of the type described in U.S. Pat. No. 3,492,330; polyisocyanates containing allophanate groups of the type described, for example, in British Pat. No. 994,890, Belgian Pat. No. 761,626 and published Dutch Patent Application No. 7,102,524; polyisocyanates containing isocyanurate groups of the type described, for example, in German Pat. Nos. 1,022,789; 1,222,067 and 1,027,394 and German Offenlegungsschrift Nos. 1,929,034 and 2,004,048; polyisocyanates containing urethane groups of the type described, for example, in Belgian Pat. No. 752,261 or U.S. Pat. No. 3,394,164; polyisocyanates containing acylated urea groups as disclosed in German Pat. No. 1,230,778; polyisocyanates containing biuret groups of the type described, for example, in British Pat. Nos. 956,474 and 1,072,956, U.S. Pat. No. 3,567,763 and German Pat. No. 1,231,688; reaction products of the aforementioned isocyanates with acetals as described in German Pat. No. 1,072,385.

It is also possible to use the distillation residues containing isocyanate groups accumulating in the commercial production of isocyanates, optionally dissolved in one or more of the aforementioned polyisocyanates. It is also possible to use mixtures of the aforementioned polyisocyanates.

In general, it is particularly preferred to use the readily accessible polyisocyanates such as 2,4- and 2,6-tolylene diisocyanate and mixtures of these isomers ("TDI"); polyphenyl polymethylene polyisocyanates, of the type obtained by aniline-formaldehyde condensation and subsequent phosgenation ("crude MDI"); and polyisocyanates containing carbodiimide groups, urethane groups, allophanate groups, isocyanurate groups, urea groups or biuret groups ("modified polyisocyanates").

According to the invention, water and/or readily volatile organic substances are often jointly used as blowing agents in the production of the polyurethane foams. Suitable organic blowing agents include halogen-substituted alkanes, such as methylene chloride, chloroform, ethylidene chloride, vinylidene chloride, monofluortrichlormethane, chlordifluormethane, and dichlordifluormethane; butane; hexane; heptane; or diethylether. A blowing effect, may also be obtained by adding compounds which decompose spontaneously at temperatures above room temperature, giving off gases such as nitrogen. Examples of such compounds include azo compounds, such as azoisobutyronitrile. Further examples of blowing agents and details of the use of blowing agents may be found in Kunststoff-Handbuch Vol. VII, published by Vieweg and Hochtlen, Carl-Hanser-Verlag, Munich 1966, for example, on pages 108 and 109, 453 to 455 and 507 to 510.

According to the invention, organometallic compounds, especially organotin compounds, may be used in combination with the catalysts of the instant invention.

Preferred organotin compounds include tin-(II)-salts of carboxylic acids, such as tin-(II)-acetate, tin-(II)-octoate, tin-(II)-ethylhexoate and tin-(II)-laurate, and the dialkyl tin salts of carboxylic acids, such as dibutyl tin diacetate, dibutyl tin dilaurate, dibutyl tin maleate or dioctyl tin diacetate.

The organotin compounds, when used are generally present in quantities of from about 0.001 to 10% by weight, based on the quantity of the organic compounds containing at least two hydrogen atoms capable of reaction with isocyanates and having molecular weights of from 400 to 10,000. If desired, other catalysts known per se, such as tertiary amines, may be added, too.

According to the invention, surface-active additives (emulsifiers and foam stabilizers) may also be used. Examples of emulsifiers include the sodium salts of castor oil sulphonates or of fatty acids or salts of fatty acids with amines, such as diethylamine/oleic acid or diethanolamine/stearic acid. Alkali or ammonium salts of sulphonic acids, such as those of dodecylbenzene sulphonic acid or dinaphthylmethane disulphonic acid, or even of fatty acids, such as ricinoleic acid, or of polymeric fatty acids, may also be used as surface-active additives.

Suitable foam stabilizers include water-soluble polyether siloxanes. These compounds are generally of such structure that a copolymer of ethylene oxide and propylene oxide is attached to a polydimethylsiloxane radical. Foam stabilizers of this type are described, for example, in U.S. Pat. No. 3,201,372, column 3, line 60 to column 4, line 3.

According to the invention, it is also possible to use reaction retarders such as hydrochloric acid or organic acid halides; cell regulators such as paraffins or fatty alcohols or dimethyl polysiloxanes; pigments or dyes; flameproofing agents such as trischlorethylphosphate or ammonium phosphate and polyphosphate; stabilizers against the effects of ageing and weather; plasticizers; substances with fungistatic and bacteriostatic effects; and fillers such as barium sulphate, kieselguhr, carbon black or prepared chalk.

Further examples of the surface-active additives and foam stabilizers optionally used in accordance with the invention, and of cell regulators, reaction retarders, stabilizers, flameproofing agents, plasticizers, dyes, fillers, substances with fungistatic and bacteriostatic effects, and also details on the way in which these additives are to be used and how they work, may be found in Kunststoff-Handbuch, Vol. VI, published by Vieweg and Hochtlen, Carl-Hanser-Verlag, Munich, 1966, for example pages 103 to 113.

According to the invention, the reaction components are reacted by the known single-stage process, by the prepolymer process or by the semi-prepolymer process, in many cases using machines of the type described, for example in U.S. Pat. No. 2,764,565. Particulars of processing equipment suitable for use in accordance with the invention may be found, for example, on pages 121 and 205 of Kunststoff-Handbuch, Vol. VI, published by Vieweg and Hochtlen, Carl-Hanser-Verlag, Munich 1966.

The end-products of the process according to the invention are flexible, semi-flexible or hard foams containing urethane groups. They are used for the applications normally reserved for products of this type. Typically, they may be used as mattresses, as upholstery material in the furniture and automobile industry, for the production of protective padding of the type used in the automobile industry, and finally as a sound-insulating material and as a heat-insulating and cold-insulating material, for example, in the building industry or in the refrigeration industry.

The invention is illustrated by the following Examples.

EXAMPLE 1

580 g (4 mols) of N,N',N''-trimethyl diethylene triamine are added dropwise at 80° C to 1632 g (16 mols) of acetic acid anhydride, followed by boiling under reflux for 6 hours. The excess acetanhydride and acetic acid is then removed in a vacuum obtained using a water pump, and the product taken up in 1 liter of acetone after neutralization with potassium carbonate. Filtration through a filter filled with potassium carbonate is followed by washing with acetone and then by distillation following removal of the acetone in a high vacuum.

Main runnings: 752 g ≙ 82% of the theoretical yield
Boiling point: 165°–171° C/0.1 mm Hg. The product was believed to be N,N''-diacetyl-N,N',N''-trimethyl diethylene triamine. IR—, NMR-spectra and elemental analysis confirmed the structure.

EXAMPLE 2

435 g (3 mols) of N,N',N''-trimethyl diethylene triamine are gradually added, while cooling with ice, to 972 g (6 mols) of dicarbonic acid diethyl ester, followed by stirring for 2 hours at a temperature rising from room temperature to 85° C. When the evolution of carbon dioxide is over, ethanol is distilled off in a vacuum obtained using a water pump up to an external temperature of 100° C, and the residue fractionated in a high vacuum.

Main runnings: 704 g ≙ 81% of the theoretical yield
Boiling point: 133°–136° C0.2 mm Hg IR—, NMR-spectra and elemental analysis confirm the structure as 2,2'-[N-methylethyl urethanol]-N-methyl diethylene amine.

EXAMPLE 3

179 g (2 mols) of diketene are added to 145 g (1 mol) of N,N',N''-trimethyl diethylene triamine, dissolved in 250 ml of acetone, at 20° to 23° C, followed by stirring at this temperature for a period of 12 hours. The acetone is then completely removed, ultimately at 60° C, in a vacuum obtained using a water pump. 2,2'-[N-methylacetyl acetamido]-N-methyl diethylene amine is obtained in a yield of 310 g ≙ 99% of the theoretical. IR— and NMR-spectra and elemental analysis confirmed the structure.

EXAMPLE 4

150 g (0.86 mol) of N,N',N''-trimethyl dipropylene triamine are added dropwise while cooling with ice to 281 g (1.73 mol) of dicarbonic acid diethyl ester, followed by heating for 10 hours to 85° C until the evolution of carbon dioxide is over. After the alcohol has been distilled off, the product is fractionated in a high vacuum.

Main runnings: 158 g ≙ 57.5% of the theoretical yield of 2,2'-[N-methylethyl urethano]-N-methyl dipropylene amine
Boiling point: 140°–142° C/0.1 mm Hg.

EXAMPLE 5

A. 50 parts by weight of a trimethylolpropane-based polypropylene glycol modified with ethylene oxide (hydroxyl number of 28) in such a way that it contained 60% of terminal primary hydroxyl groups and 50 parts by weight of a trimethylolpropane-based polypropylene glycol which had been modified with ethylene oxide in such a way that it contained more than 70% of terminal primary hydroxyl groups and which, in addition, had been grafted with acrylonitrile and styrene in a ratio of 60 : 40 and had an OH-number of 28, 2.7 parts by weight of water, 1.0 parts by weight of diazabicyclo-2,2,2-octane, 0.08 part by weight of 2,2'-dimethyl amino diethyl ether, 1.0 part by weight of an alkyl phenyl polysiloxane, 0.1 part by weight of a polyether polysiloxane, B. 0.3 parts by weight of the N,N''-diacetyl-N,N',N''-trimethyl diethylene triamine of Example 1, were mixed together and reacted with C. 32.3 parts by weight of a tolylene diisocyanate mixture (2,4- and 2,6-isomers in a ratio by weight of 80:20) and 20 parts by weight of a polyphenyl-polymethylene polyisocyanate obtained by condensing aniline with formaldehyde, followed by phosgenation.

A foam with the following mechanical properties is obtained:

| | |
|---|---|
| Gross density DIN 53 420 (kg/m³) | 39.5 |
| Tensile strength DIN 53 571 (KPa) | 160 |
| Breaking elongation DIN 53 571 (%) | 170 |
| Compressive strength DIN 53 577 (KPa) | 3.1 |

EXAMPLE 6

0.5 part by weight of 2,2'-[N-methylethyl urethanol]-N-methyl diethylene amine (cf. Example 2) are added to the polyether mixture described in Example 5 (A), including the water, stabilizer and activator, and the resulting mixture reacted with 32.3 parts by weight of polyisocyanate (C) of Example 5.

A foam with the following properties is obtained:

| | |
|---|---|
| Gross density DIN 53 420 (kg/m³) | 46 |
| Tensile strength DIN 53 571 (KPa) | 115 |
| Breaking elongation DIN 53 571 (%) | 150 |
| Compressive strength DIN 53 577 (KPa) | 3.3 |

EXAMPLE 7

0.5 part by weight of 2,2'-[N-methylacetyl acetamido]-N-methyl diethylene amine (cf. Example 3) are added to the polyether mixture described in Example 5 (A), including the water, stabilizer and activator, and the resulting mixture reacted with 32.3 parts by weight of polyisocyanate (C) of Example 5.

A foam with the following properties is obtained:

| | |
|---|---|
| Gross density DIN 53 420 (kg/m³) | 44 |
| Tensile strength DIN 53 571 (KPa) | 100 |
| Breaking elongation DIN 53 571 (%) | 130 |
| Compressive strength DIN 53 577 (KPa) | 2.7 |

EXAMPLE 8

The polyether mixture described in Example 5 (A), including the water, stabilizer and activator, is mixed with 0.5 parts by weight of 2,2'-[N-methylethyl urethano]-N-methyl dipropylene amine of Example 4, and reacted with 32.3 parts by weight of polyisocyanate (C) of Example 5.

A foam with the following properties is obtained:

| | |
|---|---|
| Gross density DIN 53 420 (kg/m³) | 42 |
| Tensile strength DIN 53 571 (KPa) | 125 |
| Breaking elongation DIN 53 571 (%) | 150 |
| Compressive strength DIN 53 577 (KPa) | 3.2 |

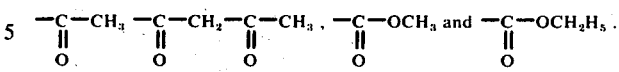

What is claimed is:

1. In a process for the production of polyurethane foams comprising reacting an organic compound containing at least two active hydrogen atoms with an organic polyisocyanate and water and/or organic blowing agents, in the presence of catalysts containing tertiary nitrogen atoms and optionally in the presence of other foam additives, the improvement wherein the catalysts used are polyacyl compounds corresponding to the general formula:

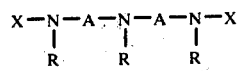

wherein
A represents a $C_1$–$C_6$ alkylene group;
R represents a $C_1$–$C_5$ alkyl group;
X represents an acyl group.

2. The process of claim 1 wherein said polyacyl compound is present in an amount of from 0.01 to 5 percent by weight based on the total weight of the foamable reaction mixture.

3. The process of claim 2 wherein the amount of polyacyl compound is from 0.1 to 1 percent by weight based on the total weight of the foamable reaction mixture.

4. The process of claim 1, wherein said catalyst is of the formula:

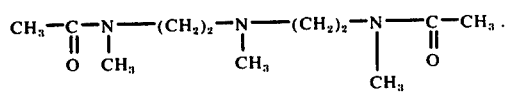

5. The process of claim 1, wherein said catalyst is of the formula:

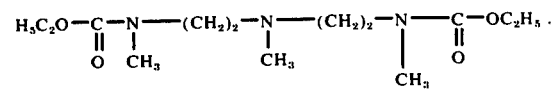

6. The process of claim 1, wherein said catalyst is of the formula:

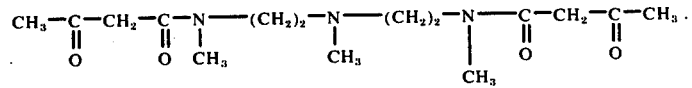

7. The process of claim 1, wherein said catalyst is of the formula:

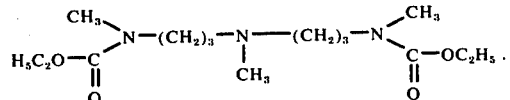

8. The process of claim 1 wherein the group A of said polyacyl compound represents an alkylene group selected from the group consisting of $C_2$ and $C_3$ alkylene groups.

9. The process of claim 1 wherein the group R in said polyacyl compound represents an alkyl group selected from the group consisting of methyl and ethyl groups.

10. The process of claim 1 wherein said X group in said polyacyl compound represents an acyl group selected from the group consisting of: